(12) United States Patent
Xicohtencatl Cortes et al.

(10) Patent No.: US 11,718,649 B2
(45) Date of Patent: Aug. 8, 2023

(54) **DIMERIC AND TRIMERIC PROTEINS BASED ON THE FIMH, CSGA, AND PAPG ADHESINS OF UROPATHOGENIC *ESCHERICHIA COLI***

(71) Applicant: HOSPITAL INFANTIL DE MÉXICO "FEDERICO GÓMEZ", Mexico City (MX)

(72) Inventors: Juan Xicohtencatl Cortes, Mexico City (MX); Victor Manuel Luna Pineda, Mexico City (MX)

(73) Assignee: HOSPITAL INFANTIL DE MÉXICO "FEDERICO GÓMEZ"

( * ) Notice: Subject to any disclaimer, the term of this patent is extended or adjusted under 35 U.S.C. 154(b) by 268 days.

(21) Appl. No.: 16/754,118

(22) PCT Filed: Oct. 11, 2018

(86) PCT No.: PCT/MX2018/000105
§ 371 (c)(1),
(2) Date: Apr. 6, 2020

(87) PCT Pub. No.: WO2019/074352
PCT Pub. Date: Apr. 18, 2019

(65) Prior Publication Data
US 2020/0369732 A1 Nov. 26, 2020

(30) Foreign Application Priority Data
Oct. 11, 2017 (MX) .................... MX/a/2017/013104

(51) Int. Cl.
*C07K 14/245* (2006.01)
*C07K 1/14* (2006.01)
*C12N 15/62* (2006.01)

(52) U.S. Cl.
CPC .............. *C07K 14/245* (2013.01); *C07K 1/14* (2013.01); *C12N 15/62* (2013.01)

(58) Field of Classification Search
CPC ......... C12N 15/62; C07K 14/245; C07K 1/14
See application file for complete search history.

(56) References Cited

U.S. PATENT DOCUMENTS

2009/0324633 A1* 12/2009 Pizza ...................... A61P 37/04
530/324

OTHER PUBLICATIONS

Luna-Pineda et al. (2016) Dimeric and Trimeric Fusion Proteins Generated with Fimbrial Adhesins of Uropathogenic *Escherichia coli*, Front. Cell. Infect. Microbiol., vol. 6, Article 135, pp. 1-15.*
NCBI_PapG_AAN82031.1 (2014) https://www.ncbi.nlm.nih.gov/protein/AAN82031, pp. 1-2.*
NCBI_FimH_AAN83822.1 (2014) https://www.ncbi.nlm.nih.goV/protein/AAN83822.1, paes 1-2.*
NCBI_CsgA_AAN79779.1 (2014) https://www.ncbi.nlm.nih.gov/protein/AAN79779.1, pp. 1-2.*
Ashkar, Ali A. et al. "FimH Adhesin of Type 1 Fimbriae Is a Potent Inducer of Innate Antimicrobial Responses Which Requires TLR4 and Type 1 Interferon Signalling," PLoS Pathogens, Dec. 2008, vol. 4, Issue 12, pp. 1-12.
Bens, Marcelle et al. "Flagellin/TLR5 signalling activates renal collecting duct cells and facilitates invasion and cellular translocation of uropathogenic *Escherichia coli*," Cellular Microbiology (2014) 16(10), pp. 1503-1517.
Datsenko, Kirill A. et al. "One-step inactivation of chromosomal genes in *Escherichia coli* K-12 using PCR products," Department of Biological Sciences, Purdue University, vol. 97, No. 12, Jun. 6, 2000, pp. 6640-6645.
Fischer, Hans et al. "Mechanism of pathogen-specific TLR4 activation in the mucosa: Fimbriae, recognition receptors and adaptor protein selection," Eur. J. Immunol. 2006, 36, pp. 267-277.
Habibi, Mehri et al. "In silico design of fusion protein of FimH from uropathogenic *Escherichia coli* and MrpH from Proteus mirabilis against urinary tract infections," Department of Molecular Biology, Advanced Biomedical Research, 2015, 4:217, pp. 1-8.
Habibi, Mehri et al. "Intranasal immunization with fusion protein MrpH•FimH and MPL adjuvant confers protection against urinary tract infections caused by uropathogenic *Escherichia coli* and Proteus mirabilis," Molecular Immunology 64, 2015, pp. 285-294.
Hannan, T.J., et al. "A Murine Model for *Escherichia coli* Urinary Tract Infection," Chapter 14, Methods Mol. Biol., 2016, pp. 159-175.
Huleatt, James W. et al. "Vaccination with recombinant fusion proteins incorporating Toll-like receptor ligands induces rapid cellular and humoral immunity," Vaccine 25, 2007, pp. 763-775.
Hung, Chia-Suei et al. "A murine model of urinary tract infection", Nature Protocols, vol. 4, No. 8, 2009, pp. 1230-1243.
Karam, Mohammad Reza Asadi et al. "Vaccination with recombinant FimH fused with flagellin enhances cellular and humoral immunity against urinary tract infection in mice," Vaccine 31, 2013, pp. 1210-1216.
Karam, Mohammad Reza Asadi et al. "Assessment of immune responses of the flagellin (FliC) fused to FimH adhesin of Uropathogenic *Escherichia coli*," Molecular Immunology 54, 2013, pp. 32-39.

(Continued)

Primary Examiner — Iqbal H Chowdhury
(74) Attorney, Agent, or Firm — Morgan. Lewis & Bockius LLP

(57) ABSTRACT

The present invention is based on the fusion of FimH, CsgA and PapG adhesins (type 1 Fimbriae, curli and P, respectively) to generate biomolecules that can be used as vaccines against UTIs. Briefly, the invention is based on the design of a fusion template gene fimH-csgA-papG-fimH-csgA and defined as fcpfc to generate the different combinations of monomeric [FimH, CsgA and PapG], dimeric [FimH-CsgA (FC), CsgA-PapG (CP) and PapG-FimH (PF)] and trimeric (FimH-PapG-CsgA (FCP), PapG-CsgA-FimH (PCF) and CsgA-FimH-PapG (CFP)] proteins. Bioactivity was determined by the antibodies present in UP sera and urine, the quantification in the release of cytokines and adhesion inhibition assays.

13 Claims, 8 Drawing Sheets
Specification includes a Sequence Listing.

(56) References Cited

OTHER PUBLICATIONS

Lane, M.C. et al. "Role of P-fimbrial-mediated adherence in pyelonephritis and persistence of uropathogenic *Escherichia coli* (UPEC) in the mammalian kidney," Kidney International 72, 2007, pp. 19-25.

Lane, M.C. et al. "Expression of flagella is coincident with uropathogenic *Escherichia coli* ascension to the upper urinary tract," Proc. Natl. Acad. Sci., Oct. 16, 2007, vol. 104, No. 42, pp. 16669-16674.

Langermann, S. et al. "Vaccination with FimH adhesin protects cynomolgus 5 monkeys from colonization and infection by uropathogenic *Escherichia coli*," J. Infect. Dis., 2000, 181, pp. 774-778.

Laskowski, Roman .A. et al. "Validation of protein models derived from experiment," Current Opinion in Structural Biology, 1998, 8, pp. 631-639.

Ledesma, Maria A. et al. "The Hemorrhagic Coli Pilus (HCP) of *Escherichia coli* O157:H7 Is an Inducer of Proinflammatory Cytokine Secretion in Intestinal Epithelial Cells," PLoS ONE, Aug. 2010, vol. 5, Issue 8, pp. 1-13.

Li, Gang et al. "Construction of a linker library with widely controllable flexibility for fusion protein design," Appl. Microbiol. Biotechnol. 100, 2016, pp. 215-225.

Martinez, Juan j. et al. "Type 1 pilus-mediated bacterial invasion of bladder epithelial cells," EMBO Journal, vol. 19, No. 12, 2000, pp. 2803-2812.

Pedretti, Alessandro et al. "VEGA—An open platform to develop chemo-bio-informatics applications, using plug-in architecture and script programming," Journal of Computer-Aided Molecular Design, 18, 2004, pp. 167-173.

Puigbò, Pere et al. "OPTIMIZER: a web server for optimizing the codon usage of DNA sequences," Nucleic Acids Research, 2007, vol. 35, pp. W126-W131.

Rapsinski, Glenn J. et al. "Toll-Like Receptor 2 and NLRP3 Cooperate To Recognize a Functional Bacterial Amyloid, Curli," Infection and Immunity, Feb. 2015, vol. 83, No. 2, pp. 693-701.

Saldaña, Zeus et al. "Synergistic role of curli and cellulose in cell adherence and biofilm formation of attaching and effacing *Escherichia coli* and identification of Fis as a negative regulator of curli," Environmental Microbiology, 2009, 11(4), pp. 992-1006.

Savar, N.S., et al. "In silico and in vivo studies of truncated forms of flagellin (FliC) of enteroaggregative *Escherichia coli* fused to FimH 5 from uropathogenic *Escherichia coli* as a vaccine candidate against urinary tract infections," Journal of Biotechnology, 2014, 175, pp. 31-37.

Sen, T.Z., Jernigan et al. "GOR V server for protein secondary structure prediction," Bioinformatics Oxf. Engl., 2005, vol. 21, No. 11, pp. 2787-2788.

Snyder, J.A. et al. "Coordinate expression of fimbriae in uropathogenic *Escherichia coli*," Infection and Immunity, Nov. 2005, vol. 73, No. 11, pp. 7588-7596.

Tükel, Çagla et al. "Toll-like receptors 1 and 2 cooperatively mediate immune responses to curli, a common amyloid from enterobacterial biofilms," Cellular Microbiology, 2010, 12, pp. 1495-1505.

Wiederstein, Markus et al. "ProSA-web: interactive web service for the recognition of errors in three-dimensional structures of proteins," Nucleic Acids Research, 2007, vol. 35, pages W407-W410.

Wilkins, M.R. et al. "Protein identification and analysis tools in the ExPASy server," The Proteomics Protocols Handbook, Methods Molecular Biology, pp. 571-607 (Note: due to size limitations, this document was uploaded in Part 1 and 2).

Yang, Jianyi et al. "I-TASSER server: new development for protein structure and function predictions," Nucleic Acids Research, 2015, vol. 43, pp. W174-W181.

Zhang, Yang et al. "TM-align: a protein structure alignment algorithm based on the TM-score," Nucleic Acids Research, 2005, vol. 33, No. 7, pp. 2302-2309.

\* cited by examiner

A

B

SEQUENCE LISTING

<160> NUMBER OF SEQ ID NOS: 9

<210> SEQ ID NO 1
<211> LENGTH: 3546
<212> TYPE: DNA
<213> ORGANISM: Artificial Sequence
<220> FEATURE:
<223> OTHER INFORMATION: fcpfc temperate gene

<400> SEQUENCE: 1

```
atgaaaaccg cgaacggtac cgcgatcccg atcggtggtg gttctgcgaa cgtttacgtt      60
aacctggcgc cggcggttaa cgttggtcag aacctggttg ttgacctgtc tacccagatc     120
ttctgccaca acgactaccc ggaaaccatc accgactacg ttaccctgca gcgtggttct     180
gcgtacggtg gtgttctgtc ttctttctct ggtaccgtta aatacaacgg ttcttcttac     240
ccgttcccga ccacctctga aaccccgcgt gttgtttaca actctcgtac cgacaaaccg     300
tggccggttg cgctgtacct gaccccggtt tcttctgcgg gtggtgttgc gatcaaagcg     360
ggttctctga tcgcggttct gatcctgcgt cagaccaaca actacaactc tgacgacttc     420
cagttcgttt ggaacatcta cgcgaacaac gacgttgttg ttccgaccgg tggttgcgac     480
gcgtctgcgc gtgacgttac cgttaccctg ccggactacc cgggttctgt tccgatcccg     540
ctgaccgttt actgcgcgaa atctcagaac ctgggttact acctgtctgg taccaccgcg     600
```

-continued

```
gacgcgggta actctatctt caccaacacc gcgtctttct ctccggcgca gggtgttggt    660
gttcagctga cccgtaacgg taccatcatc ccggcgaaca acaccgtttc tctgggtgcg    720
gttggtacct ctgcggtttc tctgggtctg accgcgaact acgcgcgtac cggtggtcag    780
gttaccgcgg gtaacgttca gtctatcatc ggtgttacct tcgtttacca ggaagcggcg    840
gcgaaagaag cggcggcgaa agaagcggcg gcgaaagaag cggcggcgaa agaagcggcg    900
gcgaaatctg aactgaacat ctaccagtac ggtggtggta actctgcgct ggcgcagcag    960
gcggacgcgc gtaactctga cctgaccatc acccagcacg gtggtggtaa cggtgcggac   1020
gttggtcagg gttctgacga ctcttctatc gacctgaccc agcgtggttt cggtaactct   1080
gcgaccctgg accagtggaa cggtaaagac tctaccatga ccgttaaaca gttcggtggt   1140
ggtaacggtg cggcggttga ccagaccgcg tctaactctt ctgttaacgt tacccaggtt   1200
ggtttcggta caacgcgac cgcgcaccag tacgaagcgg cggcgaaaga agcggcggcg    1260
aaagaagcgg cggcgaaaga agcggcggcg aaagaagcgg cggcgaaatc tctgggtaac   1320
gttaactctt accagggtgg taacgttgtt atcacccagc gtccgcagtt catcacctct   1380
tggcgtccgg gtatcgcgac cgttacctgg aaccagtgca acgtccgga attcgcggac    1440 ggttcttggg cgtactaccg tgaatacatc gcgtgggttg ttttcccgaa aaagttatg    1500 accaaaaacg ttacccgct gttcatcgaa gttcacaaca aggttcttg gtctgaagaa     1560 aacaccggtg acaacgactc ttacttcttc ctgaaaggtt acaaatggga cgaacgtgcg   1620
ttcgacgcgg gtaacctgtg ccagaaaccg ggtgaaacca cccgtctgac cgaaaaattc   1680
aacgacatca tcttcaaagt tgcgctgccg gcggacctgc cgctgggtga ctactctgtt   1740
accatcccgt acacctctgg tatccagcgt cacttcgcgt cttacctggg tgcgcgtttc   1800
aaaatcccgt acaacgttgc gaaaaccctg ccgcgtgaaa acgaaatgct gttcctgttc   1860
aaaaacatcg gtggttgccg tccgtctgcg cagtctctgg aaatcaaaca cggtgacctg   1920
tctatcaact ctgcgaacaa ccactacgcg gcgcagaccc tgtctgtttc ttgcgacgtt   1980
ccggcgaaca tccgtttcat gctgctgcgt aacaccaccc cgacctactc tcacggtaaa   2040
aaattctctg ttggtctggg tcacggttgg gactctatcg tttctgttaa cggtgttgac   2100
accggtgaaa ccaccatgcg ttggtacaaa gcgggtaccc agaacctgac catcggttct   2160
cgtctgtacg gtgaatcttc taaaatccag ccgggtgttc tgtctggttc tgcgaccctg   2220
ctgatgatcc tgccgggcga agcggcggcg aaagaagcgg cggcgaaaga agcggcggcg   2280
aaagaagcgg cggcgaaaga agcggcggcg aaaaaaaccg cgaacggtac cgcgatcccg   2340
atcggtggtg gttctgcgaa cgtttacgtt aacctggcgc cggcggttaa cgttggtcag   2400
aacctggttg ttgacctgtc tacccagatc ttctgccaca acgactaccc ggaaaccatc   2460
accgactacg ttaccctgca gcgtggttct gcgtacggtg gtgttctgtc ttctttctct   2520
ggtaccgtta aatacaacgg ttcttcttac ccgttcccga ccacctctga aaccccgcgt   2580
gttgtttaca ctctcgtac cgacaaaccg tggccggttg cgctgtacct gaccccggtt    2640
tcttctgcgg gtggtgttgc gatcaaagcg ggttctctga tcgcggttct gatcctgcgt   2700
cagaccaaca actacaactc tgacgacttc agttcgtttt ggaacatcta cgcgaacaac   2760
gacgttgttg ttccgaccgg tggttgcgac gcgtctgcgc gtgacgttac cgttaccctg   2820
ccggactacc cggggtctgt tccgatcccg ctgaccgttt actgcgcgaa atctcagaac   2880
ctgggttact acctgtctgg taccaccgcg gacgcgggta actctatctt caccaacacc   2940
gcgtctttct ctccggcgca gggtgttggt gttcagctga cccgtaacgg taccatcatc   3000
```

```
ccggcgaaca acaccgtttc tctgggtgcg gttggtacct ctgcggtttc tctgggtctg    3060
accgcgaact acgcgcgtac cggtggtcag gttaccgcgg gtaacgttca gtctatcatc    3120
ggtgttacct tcgtttacca ggaagcggcg gcgaaagaag cggcggcgaa agaagcggcg    3180
gcgaaagaag cggcggcgaa agaagcggcg gcgaaatctg aactgaacat ctaccagtac    3240
ggtggtggta actctgcgct ggcgcagcag gcggacgcgc gtaactctga cctgaccatc    3300
acccagcacg gtggtggtaa cggtgcggac gttggtcagg ttctgacga ctcttctatc    3360 gacctgaccc agcgtggttt cggtaactct gcgaccctgg accagtggaa cggtaaagac    3420
tctaccatga ccgttaaaca gttcggtggt ggtaacggtg cggcggttga ccagaccgcg    3480
tctaactctt ctgttaacgt tacccaggtt ggtttcggta acaacgcgac cgcgcaccag    3540
tactaa                                                                3546
```

<210> SEQ ID NO 2
<211> LENGTH: 1181
<212> TYPE: PRT
<213> ORGANISM: Artificial Sequence
<220> FEATURE:
<223> OTHER INFORMATION: template fcpfc

<400> SEQUENCE: 2

```
Met Lys Thr Ala Asn Gly Thr Ala Ile Pro Ile Gly Gly Gly Ser Ala
1               5                   10                  15

Asn Val Tyr Val Asn Leu Ala Pro Ala Val Asn Val Gly Gln Asn Leu
            20                  25                  30

Val Val Asp Leu Ser Thr Gln Ile Phe Cys His Asn Asp Tyr Pro Glu
        35                  40                  45

Thr Ile Thr Asp Tyr Val Thr Leu Gln Arg Gly Ser Ala Tyr Gly Gly
    50                  55                  60

Val Leu Ser Ser Phe Ser Gly Thr Val Lys Tyr Asn Gly Ser Ser Tyr
65                  70                  75                  80

Pro Phe Pro Thr Thr Ser Glu Thr Pro Arg Val Val Tyr Asn Ser Arg
                85                  90                  95

Thr Asp Lys Pro Trp Pro Val Ala Leu Tyr Leu Thr Pro Val Ser Ser
            100                 105                 110

Ala Gly Gly Val Ala Ile Lys Ala Gly Ser Leu Ile Ala Val Leu Ile
        115                 120                 125

Leu Arg Gln Thr Asn Asn Tyr Asn Ser Asp Asp Phe Gln Phe Val Trp
    130                 135                 140

Asn Ile Tyr Ala Asn Asn Asp Val Val Val Pro Thr Gly Gly Cys Asp
145                 150                 155                 160

Ala Ser Ala Arg Asp Val Thr Val Thr Leu Pro Asp Tyr Pro Gly Ser
                165                 170                 175

Val Pro Ile Pro Leu Thr Val Tyr Cys Ala Lys Ser Gln Asn Leu Gly
            180                 185                 190

Tyr Tyr Leu Ser Gly Thr Thr Ala Asp Ala Gly Asn Ser Ile Phe Thr
        195                 200                 205

Asn Thr Ala Ser Phe Ser Pro Ala Gln Gly Val Gly Val Gln Leu Thr
    210                 215                 220

Arg Asn Gly Thr Ile Ile Pro Ala Asn Asn Thr Val Ser Leu Gly Ala
225                 230                 235                 240

Val Gly Thr Ser Ala Val Ser Leu Gly Leu Thr Ala Asn Tyr Ala Arg
                245                 250                 255
```

-continued

```
Thr Gly Gly Gln Val Thr Ala Gly Asn Val Gln Ser Ile Ile Gly Val
            260                 265                 270

Thr Phe Val Tyr Gln Glu Ala Ala Lys Glu Ala Ala Lys Glu
        275                 280                 285

Ala Ala Ala Lys Glu Ala Ala Ala Lys Glu Ala Ala Lys Ser Glu
    290                 295                 300

Leu Asn Ile Tyr Gln Tyr Gly Gly Asn Ser Ala Leu Ala Gln Gln
305                 310                 315                 320

Ala Asp Ala Arg Asn Ser Asp Leu Thr Ile Thr Gln His Gly Gly Gly
                325                 330                 335

Asn Gly Ala Asp Val Gly Gln Gly Ser Asp Ser Ser Ile Asp Leu
            340                 345                 350

Thr Gln Arg Gly Phe Gly Asn Ser Ala Thr Leu Asp Gln Trp Asn Gly
        355                 360                 365

Lys Asp Ser Thr Met Thr Val Lys Gln Phe Gly Gly Asn Gly Ala
    370                 375                 380

Ala Val Asp Gln Thr Ala Ser Asn Ser Ser Val Asn Val Thr Gln Val
385                 390                 395                 400

Gly Phe Gly Asn Asn Ala Thr Ala His Gln Tyr Glu Ala Ala Ala Lys
                405                 410                 415

Glu Ala Ala Ala Lys Glu Ala Ala Lys Glu Ala Ala Ala Lys Glu
            420                 425                 430

Ala Ala Ala Lys Ser Leu Gly Asn Val Asn Ser Tyr Gln Gly Gly Asn
        435                 440                 445

Val Val Ile Thr Gln Arg Pro Gln Phe Ile Thr Ser Trp Arg Pro Gly
    450                 455                 460

Ile Ala Thr Val Thr Trp Asn Gln Cys Asn Gly Pro Glu Phe Ala Asp
465                 470                 475                 480

Gly Ser Trp Ala Tyr Tyr Arg Glu Tyr Ile Ala Trp Val Val Phe Pro
                485                 490                 495

Lys Lys Val Met Thr Lys Asn Gly Tyr Pro Leu Phe Ile Glu Val His
            500                 505                 510

Asn Lys Gly Ser Trp Ser Glu Glu Asn Thr Gly Asp Asn Asp Ser Tyr
        515                 520                 525

Phe Phe Leu Lys Gly Tyr Lys Trp Asp Glu Arg Ala Phe Asp Ala Gly
    530                 535                 540

Asn Leu Cys Gln Lys Pro Gly Glu Thr Thr Arg Leu Thr Glu Lys Phe
545                 550                 555                 560

Asn Asp Ile Ile Phe Lys Val Ala Leu Pro Ala Asp Leu Pro Leu Gly
                565                 570                 575

Asp Tyr Ser Val Thr Ile Pro Tyr Thr Ser Gly Ile Gln Arg His Phe
            580                 585                 590

Ala Ser Tyr Leu Gly Ala Arg Phe Lys Ile Pro Tyr Asn Val Ala Lys
        595                 600                 605

Thr Leu Pro Arg Glu Asn Glu Met Leu Phe Leu Phe Lys Asn Ile Gly
    610                 615                 620

Gly Cys Arg Pro Ser Ala Gln Ser Leu Glu Ile Lys His Gly Asp Leu
625                 630                 635                 640

Ser Ile Asn Ser Ala Asn Asn His Tyr Ala Ala Gln Thr Leu Ser Val
                645                 650                 655

Ser Cys Asp Val Pro Ala Asn Ile Arg Phe Met Leu Leu Arg Asn Thr
            660                 665                 670
```

-continued

```
Thr Pro Thr Tyr Ser His Gly Lys Lys Phe Ser Val Gly Leu Gly His
            675                 680                 685

Gly Trp Asp Ser Ile Val Ser Val Asn Gly Val Asp Thr Gly Glu Thr
    690                 695                 700

Thr Met Arg Trp Tyr Lys Ala Gly Thr Gln Asn Leu Thr Ile Gly Ser
705                 710                 715                 720

Arg Leu Tyr Gly Glu Ser Ser Lys Ile Gln Pro Gly Val Leu Ser Gly
                725                 730                 735

Ser Ala Thr Leu Leu Met Ile Leu Pro Gly Glu Ala Ala Lys Glu
            740                 745                 750

Ala Ala Ala Lys Glu Ala Ala Ala Lys Glu Ala Ala Lys Glu Ala
            755                 760                 765

Ala Ala Lys Lys Thr Ala Asn Gly Thr Ala Ile Pro Ile Gly Gly Gly
            770                 775                 780

Ser Ala Asn Val Tyr Val Asn Leu Ala Pro Ala Val Asn Val Gly Gln
785                 790                 795                 800

Asn Leu Val Val Asp Leu Ser Thr Gln Ile Phe Cys His Asn Asp Tyr
            805                 810                 815

Pro Glu Thr Ile Thr Asp Tyr Val Thr Leu Gln Arg Gly Ser Ala Tyr
            820                 825                 830

Gly Gly Val Leu Ser Ser Phe Ser Gly Thr Val Lys Tyr Asn Gly Ser
            835                 840                 845

Ser Tyr Pro Phe Pro Thr Thr Ser Glu Thr Pro Arg Val Val Tyr Asn
850                 855                 860

Ser Arg Thr Asp Lys Pro Trp Pro Val Ala Leu Tyr Leu Thr Pro Val
865                 870                 875                 880

Ser Ser Ala Gly Gly Val Ala Ile Lys Ala Gly Ser Leu Ile Ala Val
            885                 890                 895

Leu Ile Leu Arg Gln Thr Asn Asn Tyr Asn Ser Asp Asp Phe Gln Phe
            900                 905                 910

Val Trp Asn Ile Tyr Ala Asn Asn Asp Val Val Pro Thr Gly Gly
            915                 920                 925

Cys Asp Ala Ser Ala Arg Asp Val Thr Val Thr Leu Pro Asp Tyr Pro
930                 935                 940

Gly Ser Val Pro Ile Pro Leu Thr Val Tyr Cys Ala Lys Ser Gln Asn
945                 950                 955                 960

Leu Gly Tyr Tyr Leu Ser Gly Thr Thr Ala Asp Ala Gly Asn Ser Ile
            965                 970                 975

Phe Thr Asn Thr Ala Ser Phe Ser Pro Ala Gln Gly Val Gly Val Gln
            980                 985                 990

Leu Thr Arg Asn Gly Thr Ile Ile Pro Ala Asn Asn Thr Val Ser Leu
            995                 1000                1005

Gly Ala Val Gly Thr Ser Ala Val Ser Leu Gly Leu Thr Ala Asn
        1010                1015                1020

Tyr Ala Arg Thr Gly Gly Gln Val Thr Ala Gly Asn Val Gln Ser
        1025                1030                1035

Ile Ile Gly Val Thr Phe Val Tyr Gln Glu Ala Ala Ala Lys Glu
        1040                1045                1050

Ala Ala Ala Lys Glu Ala Ala Lys Glu Ala Ala Ala Lys Glu
        1055                1060                1065

Ala Ala Ala Lys Ser Glu Leu Asn Ile Tyr Gln Tyr Gly Gly Gly
        1070                1075                1080
```

```
Asn Ser Ala Leu Ala Gln Gln Ala Asp Ala Arg Asn Ser Asp Leu
    1085                1090                1095

Thr Ile Thr Gln His Gly Gly Asn Gly Ala Asp Val Gly Gln
    1100                1105                1110

Gly Ser Asp Asp Ser Ser Ile Asp Leu Thr Gln Arg Gly Phe Gly
    1115                1120                1125

Asn Ser Ala Thr Leu Asp Gln Trp Asn Gly Lys Asp Ser Thr Met
    1130                1135                1140

Thr Val Lys Gln Phe Gly Gly Asn Gly Ala Ala Val Asp Gln
    1145                1150                1155

Thr Ala Ser Asn Ser Ser Val Asn Val Thr Gln Val Gly Phe Gly
    1160                1165                1170

Asn Asn Ala Thr Ala His Gln Tyr
    1175                1180

<210> SEQ ID NO 3
<211> LENGTH: 58
<212> TYPE: DNA
<213> ORGANISM: Artificial Sequence
<220> FEATURE:
<223> OTHER INFORMATION: FimH-F primer

<400> SEQUENCE: 3
agaaggagat ataactatga aaccgcgaa cggtaccgcg atcccgatcg gtggtggt      58

<210> SEQ ID NO 4
<211> LENGTH: 57
<212> TYPE: DNA
<213> ORGANISM: Artificial Sequence
<220> FEATURE:
<223> OTHER INFORMATION: FimH-R primer

<400> SEQUENCE: 4
gtggtggtga tggtgatggc cctggtaaac gaaggtaaca ccgatgatag actgaac      57

<210> SEQ ID NO 5
<211> LENGTH: 53
<212> TYPE: DNA
<213> ORGANISM: Artificial Sequence
<220> FEATURE:
<223> OTHER INFORMATION: CsgA-F primer

<400> SEQUENCE: 5
agaaggagat ataactatgt ctgaactgaa catctaccag tacggtggtg gta           53

<210> SEQ ID NO 6
<211> LENGTH: 51
<212> TYPE: DNA
<213> ORGANISM: Artificial Sequence
<220> FEATURE:
<223> OTHER INFORMATION: CsgA-R primer

<400> SEQUENCE: 6
gtggtggtga tggtgatggc cgtactggtg cgcggtcgcg ttgttaccga a             51

<210> SEQ ID NO 7
<211> LENGTH: 54
<212> TYPE: DNA
<213> ORGANISM: Artificial Sequence
<220> FEATURE:
<223> OTHER INFORMATION: PapG-F primer
```

```
<400> SEQUENCE: 7
agaaggagat ataactatgt ctctgggtaa cgttaactct taccagggtg gtaa            54

<210> SEQ ID NO 8
<211> LENGTH: 53
<212> TYPE: DNA
<213> ORGANISM: Artificial Sequence
<220> FEATURE:
<223> OTHER INFORMATION: PapG-R primer

<400> SEQUENCE: 8
gtggtggtga tggtgatggc ccggcaggat catcagcagg gtcgcagaac cag             53

<210> SEQ ID NO 9
<211> LENGTH: 5
<212> TYPE: PRT
<213> ORGANISM: Artificial Sequence
<220> FEATURE:
<223> OTHER INFORMATION: Fusion of the FimH, CsgA, and PapG proteins

<400> SEQUENCE: 9

Glu Ala Ala Ala Lys
1               5
```

DIMERIC AND TRIMERIC PROTEINS BASED ON THE FIMH, CSGA, AND PAPG ADHESINS OF UROPATHOGENIC ESCHERICHIA COLI

CROSS-REFERENCE TO RELATED APPLICATIONS

This application is a U.S. national phase application of a PCT Application No. PCT/MX2018/000105 filed on Oct. 11, 2018, which claims priority to a Mexican Patent Application No. MX/a/2017/013104 filed in Mexico on Oct. 11, 2017, the disclosure of which is incorporated herein by reference in its entirety.

FIELD OF THE INVENTION

The present invention is focused on the generation of fusion proteins that can be used for diagnosis and/or as vaccines against urinary tract infections (UTIs). These fusion proteins can be dimeric or trimeric, and are based on the FimH, CsgA, and PapG adhesins of uropathogenic *Escherichia coli* (UPEC) which is the main causative agent of urinary tract infections UTIs.

REFERENCE TO A "SEQUENCE LISTING," A TABLE, OR A COMPUTER PROGRAM LISTING APPENDIX SUBMITTED ELECTRONICALLY

The sequence listing contained in the file named "116384-5004-US-CorrectedSequenceListing_ST25" and having a size of 20,480 kilobytes has been submitted electronically on Feb. 22, 2023 via EFS-Web, and the contents of the .txt file are hereby incorporated by reference in their entirety.

BACKGROUND OF THE INVENTION

The UTIs are distributed worldwide, and currently there is no effective vaccine that allows its eradication or reduces morbidity. Recombinant proteins generated by fusion technology for the incorporation of antigens of one or more pathogens have conferred a greater immune response and protection in animal models against UTIs (Asadi Karam et al., 2013; Habibi et al., 2015a, 2015b; Karam et al., 2013; Savar et al., 2014). Vaccination with a recombinant protein FimH fused with FliC, the main component of the flagellum, has shown an increase in the cellular and humoral immune response against UTIs in the murine model. High levels of IgG1 and IgG2a antibodies and a stimulation of Th1 and Th2 type T cells [INF-γ and IL (interleukin)-4] were identified after subcutaneous immunization (Asadi Karam et al., 2013). The incorporation of ligands for the "Toll" receptor (TLR) can result in a safe vaccine with greater efficacy, being equal or better to those formulated with adjuvant. Fusion proteins that include Pathogen-Associated Molecular Patterns (PAMP) induce a specific, potent and rapid response in the absence of adjuvant (Huleatt et al., 2007). TLR4 is activated by the interaction with the FimH protein by an α-mannosylated co-receptor, stimulating the MyD88-NFκB pathway, which allows the release of IL-6 and IL-8. Additionally, the FliC protein can interact as a PAMP and specifically activate TLR5, allowing the enhanced stimulation of the immune response (Bens et al., 2014). However, the mutation in the fliC gene only leads to the loss of mobility and its subsequent ascent of uropathogenic *Escherichia coli* (UPEC) from the bladder to the kidneys (Lane et al., 2007). Therefore, immunization with FliC does not generate protection in the bladder (Asadi Karam et al., 2013). Type 1 fimbriae FimH adhesin is related to the interaction of uroepithelium, facilitating adherence, colonization and invasion in the urinary tract (Ashkar et al., 2008, Martinez et al., 2000). Additionally, an immunogenic response is elicited by FimH, but with limited protection against UPEC colonization, probably due to the expression of other fimbriae (Langermann et al., 2000; Snyder et al., 2005). For this reason, we decided to fuse both adhesins, PapG of P fimbriae and CsgA of curli to the FimH adhesin that allows generating dimeric and trimeric fusion proteins. PapG adhesin is related to pyelonephritis due to the interaction of glycosphingolipids (GLS) present in kidney cells; jointly, it can promote the Tram/Trif-NFκB pathway for the release of IL-6, IL-8 by interaction with TLR4 using a GLS co-receptor (Fischer et al., 2006; Lane and Mobley, 2007). CsgA adhesin, another protein with adhesion properties, can interact with the TLR1/TLR2 complex, generating a greater stimulation in the release of IL-6 and IL-8 via the MyD88-NFκB pathway (Rapsinski et al., 2015; Tükel et al., 2010). The interaction of pattern recognition receptors with the fusion proteins generated from different adhesins (FimH, CsgA and PapG), will serve as antigens and as an adjuvant for the rapid and efficient activation of the immune system.

DESCRIPTION OF THE SEQUENCES

SEQ. ID. NO. 1. Nucleotide sequence of the fcpfc temperate gene and its translation into amino acids.
SEQ. ID. NO. 2. Amino acid sequence of the template fcpfc, corresponding to SEQ ID NO.1.
SEQ. ID. NO. 3. FimH-F primer
SEQ. ID. NO. 4. FimH-R primer
SEQ. ID. NO. 5. CsgA-F primer
SEQ. ID. NO. 6. CsgA-R primer
SEQ. ID. NO. 7. PapG-F primer
SEQ. ID. NO. 8. PapG-R primer
SEQ. ID. NO. 9. EAAAK

BRIEF DESCRIPTION OF THE INVENTION

The invention focused on the generation of fusion proteins using the FimH adhesin located in the distal part of type 1 fimbriae and the PapG adhesin of P fimbriae; as well as the structural protein CsgA of curli. All adhesins are present and are expressed in vivo in UPEC; which is the main causal agent of UTIs. Initially, the invention was focused on a fcpfc template fusion gene and with the combination of primers it was possible to generate the different monomeric, dimeric and trimeric genes for cloning. Subsequently, the fusion proteins FC (44.9 kDa) and FCP (82.1 kDa) were generated based on a bioinformatic analysis (stability, folding and antigenicity). FC and FCP fusion proteins can be considered as potential biomolecules for a functional vaccine against UTIs. Additionally, the fusion proteins can be used in vaccines without adjuvants due to their ability to stimulate the release of IL-6 and IL-8 by FimH, CsgA and PapG adhesins. The determination of antibodies in sera and urines of UTI-P against the fusion proteins showed high levels of antibodies of the IgA type and to a lesser extent the IgG type. Finally, the antibodies obtained from rabbit against the fusion proteins generated protection against the adherence of UPEC to the bladder cells in vitro.

DETAILED DESCRIPTION OF THE INVENTION

Figure 1:
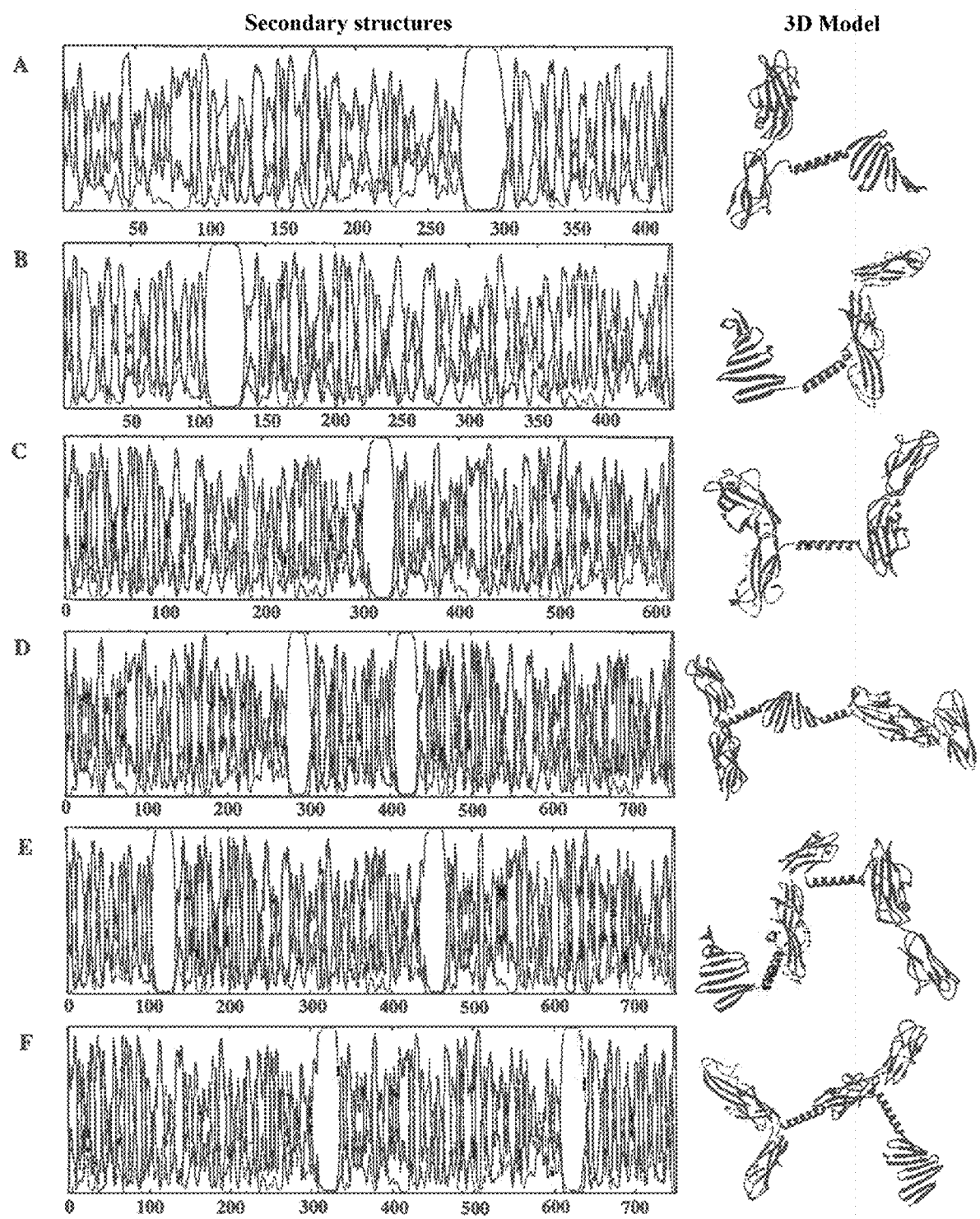
FIG. 1. Prediction of the secondary and tertiary structures of the fusion proteins: A) FC protein; B) CP protein; C) PF protein; D) FCP protein; E) CPF protein; F) PFC protein.

Analysis of the primary, secondary and tertiary structure of proteins. The sequences of the FimH, CsgA and PapG proteins of E. coli strain CFT073 were obtained from the NCBI database (ncbi.nlm.nih.gov/protein) with Accession Numbers AAN83822.1, AAN79779.1 and AAN82031.1, respectively. The signal peptide prediction was performed for each of the proteins using the SignalP 4.1 server; in addition, five repetitions of the EAAAK (SEQ. ID. NO. 9) sequence were used to carry out the fusion of the FimH, CsgA, and PapG proteins (Li et al., 2016). Molecular weight, theoretical isoelectric point, amino acid composition, estimation of the half-life, aliphatic index and "grand average of hydropathicity" (GRAVY) of the proteins were determined using the ExPASy ProtParam program (Wilkins et al., 1999). The codon adaptation index (CAI) and the guanine and cytosine (GC) content of the genes were determined using the OPTIMIZER program (Puigbò et al., 2007). The prediction of the secondary structure of the proteins was generated with the GORIV program (Sen et al., 2005). The three-dimensional (3D) modeling of the proteins was performed using the I-TASSER server and visualized with the PyMOL program (Yang et al., 2015). The 3D structures were refined and minimized using the KoBaMIN (csb.stanford.edu/kobamin/) and VegaZZ (NAMD) programs (Pedretti et al., 2004). The 3D models were validated by the "Protein Structure Analysis" (ProSA) program that allowed to determine the Z-score and the Ramachandran graph using the PROCHECK program (Laskowski et al., 1998, Wiederstein and Sippl, 2007). The 3D structures of the proteins were compared with X-ray resolved structures of the mannose binding domain of FimH (Protein Data Bank; 1TR7) and the PapG lectin domain (PDB; 1J8R), which was calculated on "Root Mean Square Deviation" (RMSD) using the TM-align program (Zhang and Skolnick, 2005). Secondary structures and 3D models are described in FIG. 1.

Epitope prediction and antigen presentation. The immune response was theoretically determined to establish variants of the proteins with ability to generate a better response. The primary and secondary structures of the proteins were used to determine linear B cell epitopes with the bcPred server (imtech.res.in/raghava/abcpred/) and peptides with affinity to the main histocompatibility complex (MHC) class II were identified with the NetMHCII program (cbs.dtu.dk/services/NetMHCII/). The 3D structure of the proteins was used to determine conformational epitopes using the Discotope server (cbs.dtu.dk/services/DiscoTope/).

Figure 2:
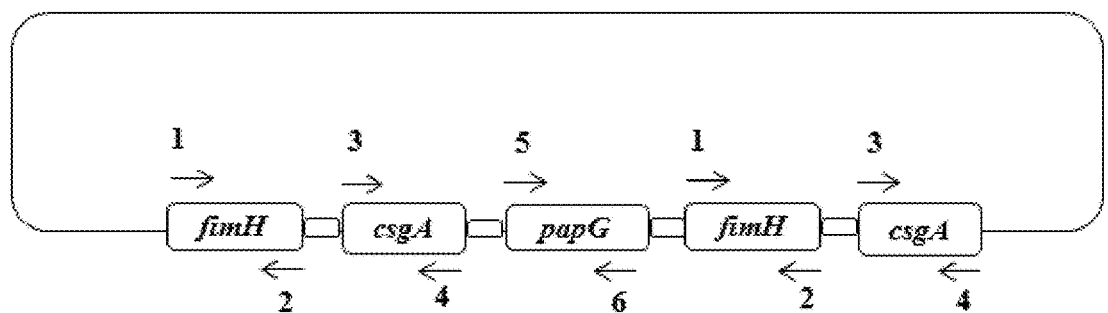
FIG. 2. A) Gene sequence of the template fimH-csgA-papG-fimH-csgA (fcpfc); B) Generation of the dimeric and trimeric fusion and monomeric genes; which are abbreviated with the first letter of fimH (f), csgA (c), and papG (p).
Figure 2:
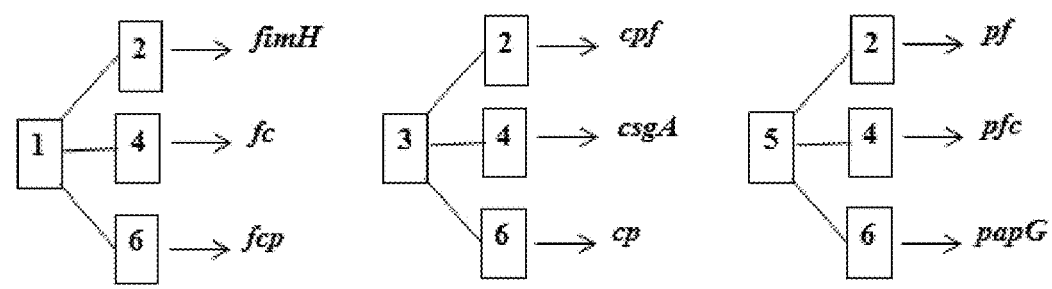

Analysis and synthesis of the fusion template gene. The sequences of fimH, csgA, and papG of the E. coli strain CFT073 were obtained with Accession Numbers GQ487191.1, NC_004431.1 and AF447814.1, respectively. Conserved sequences were compared with several UPEC strains (UTI89, ABU83972, NA114, UPEC26-1, CF-088, CF-468, IA2 and AD110 isolates) using BLAST (blast.ncbi.nlm.nih.gov/Blast.cgi) and ClustalOmega (ebi.ac.uk/Tools/msa/clustalo/) programs. Consensus nucleotide sequences were fused with the appropriate codons of the EAAAK (SEQ. ID. NO. 9) repeats to generate a fcpfc template fusion gene. The fcpfc template codons were optimized using the OPTIMIZER program (genomes.urv.es/OPTIMIZER/) and for predicting the secondary structure of the monomeric, dimeric and trimeric genes the Mfold program (unafold.rna.albany.edu/?q=mfold/RNA-Folding-Form) was used. The optimized fusion template gene was added to two cutting sites, in the 5' BamHI and the 3' SacI and this was chemically synthesized by the manufacturer GenScript (Piscataway, N.J., USA). Subsequently, it was cloned into the pUC57 vector and used for the amplification of the monomeric, dimeric and trimeric genes using specific primers. The strategy for the generation of the fusion genes using the fcpfc template is described in FIG. 2.

Figure 3:
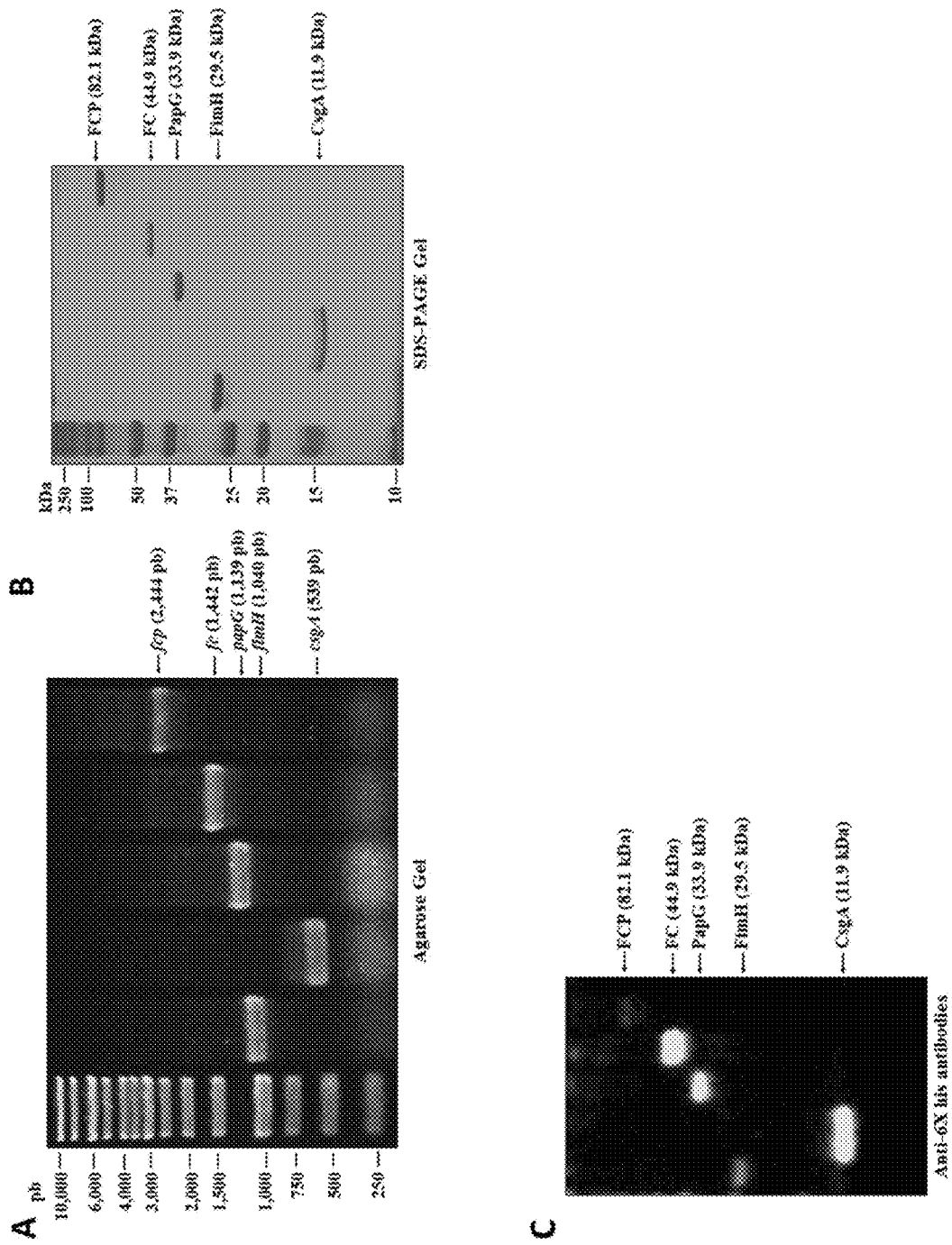
FIG. 3. Generation of fusion proteins. (A) Magnifications of fusion genes by PCR in colony; B) Purification of the fusion proteins by affinity chromatography; (C) Identification of fusion proteins by Western Blot assay.

Cloning of the genes in the expression pLATE31 vector. The design of primers for the amplification of monomeric, dimeric and trimeric genes, which were specific and with a consensus site were manually generated following the protocol of "aICator 1IC Cloning and Expression handbook" (Thermo Fisher Scientific, Waltham, Mass., USA) and synthesized by the manufacturer IDT Technologies (Coralville, Iowa, USA). The amplification of the genes was generated from "Polymerase Chain Reaction" (PCR) using the Pfu DNA polymerase from Thermo Fisher Scientific. The amplification and cloning conditions were determined from aLICator system protocols. The expression vector pLATE31 was used for the cloning of the previously amplified genes and the E. coli BL21 strain (DE3) for the transformation of the resulting vectors by electroporation. Additionally, the genes in the expression vector were verified by "next-generation sequencing" in a NexSeq 500 system (Illumina, San Diego, Calif., USA). The specific sequencing primers were obtained from the "aICator LIC Cloning and Expression Kit" and the resulting sequences were analyzed by BLAST. The colony PCR verification of E. coli BL21 transformants are shown in FIG. 3, section (A).

Expression and purification of proteins. E. coli BL21 strain transformed with its respective expression vector pLATE31 was plated on Luria Bertani agar (LB, Becton-Dickinson, Franklin Lakes, N.J., USA) and incubated for 16 h at 30° C. The probable transformant colonies were verified by the "colony-blotting" method using an HRP anti-6× His antibody (C-Term) (Abcam, Cambridge, Mass., USA). The solubility was carried out following the protocols established by the manual of "the QIAexpressionist" of Qiagen (Jacques-Schiesser-Str, Stockach, Germany). The expression and purification of the proteins was carried out in 500 mL of LB medium supplemented with 1 mM IPTG and incubated for 5 h at 37° C. After centrifugation at 5000 rpm for 10 min, the cell pellet was resuspended in buffer A (10 mM $K_2HPO_4$, pH7.4, 150 mM NaCl and 1 mM EDTA) supplied with phenyl-methyl-sulfonyl fluoridine (PMSF; Sigma-AldrichCorp., St. Louis, Mo., USA), lysed by sonication and ultracentrifuged at 20,000 rpm for 20 min. The supernatant was removed and the pellet resuspended in buffer B (8M guanidine hydroxychloride, 100 mM NaCl and 100 mM $K_2HPO_4$, pH8). After three days of incubation at room temperature, the lysates were ultracentrifuged at 30,000 g. The supernatant was incubated in a column containing nitrile triacetyl-nickel acid agarose (Qiagen) at 4° C. for 1 h, washed with buffer C (8.5M urea, 20 mM Tris, pH7.5, 160 mM NaCl and 20 mM imidazole) and eluted with buffer D (8M urea, 50 mM $Na_2HPO_4$, pH8, 100 mM NaCl and 500 mM imidazole). The collected proteins were refolded using dialysis against a gradient of 7 to 1M urea in buffer E (25 mM Tris, pH7.5, 100 mM NaCl and 0.5 mM EDTA); the incubation was generated at 4° C. for 24 hours. The refolded proteins were stored in buffer E at −70° C. for later use.

Characterization of proteins. The proteins were quantified following the 2D-Quant kit (GE Healthcare Bio-Sciences AB, Björkgatan, Uppsala, Sweden) protocol, separated by electrophoresis in polyacrylamide gels under 14% SDS denaturing conditions (SDS-PAGE), visualized by Coomassie staining and identified by mass spectroscopy using a 4800 MALDI TOF/TOF™ analyzer (Applied Biosystems/MDSSCIEX, Waltham, Mass., USA). The CsgA protein was treated with 88% formic acid (Sigma-Aldrich Corp., St. Louis, Mo., USA) before SDS-PAGE (Saldaña et al., 2009). The molecular weight was estimated using the gel image and the Image Lab version 5.2 program from Bio-Rad (Hercules, Calif., USA). The aggregation state of the proteins was determined by dynamic light scattering (DLS) using a Zetasizer Helix equipment (Malvern Instruments Ltd, Grovewood Road, Worcestershire, United Kingdom). Gels that included the proteins were transferred into polyvinyldylene difluoridine (PVDF) membranes to confirm by Western blot assays using HRP anti-6 His (C-Terminal) antibodies (Abcam, Cambridge, Mass., USA) as previously described (Ledesma et al., 2010). The endotoxin levels (LPS) of the proteins were determined using the Pierce™ LAL Chromogenic Endotoxin Quantitation system according to the protocols established by the manufacturer (Thermo Fisher Scientific, Waltham, Mass., USA). The proteins were treated with 50 μg/mL of polymyxin B (Sigma-Aldrich Corp., St. Louis, Mo., USA) for 12 h at 4° C. before the bioactivity assays. The visualization of the fusion proteins in polyacrylamide gels and stained with Coomassie blue are shown in FIG. 3, section (B). Additionally, the identification of the fusion proteins by Western blot using specific antibodies against the histidine tag are visualized in FIG. 3, section (C).

Figure 4:
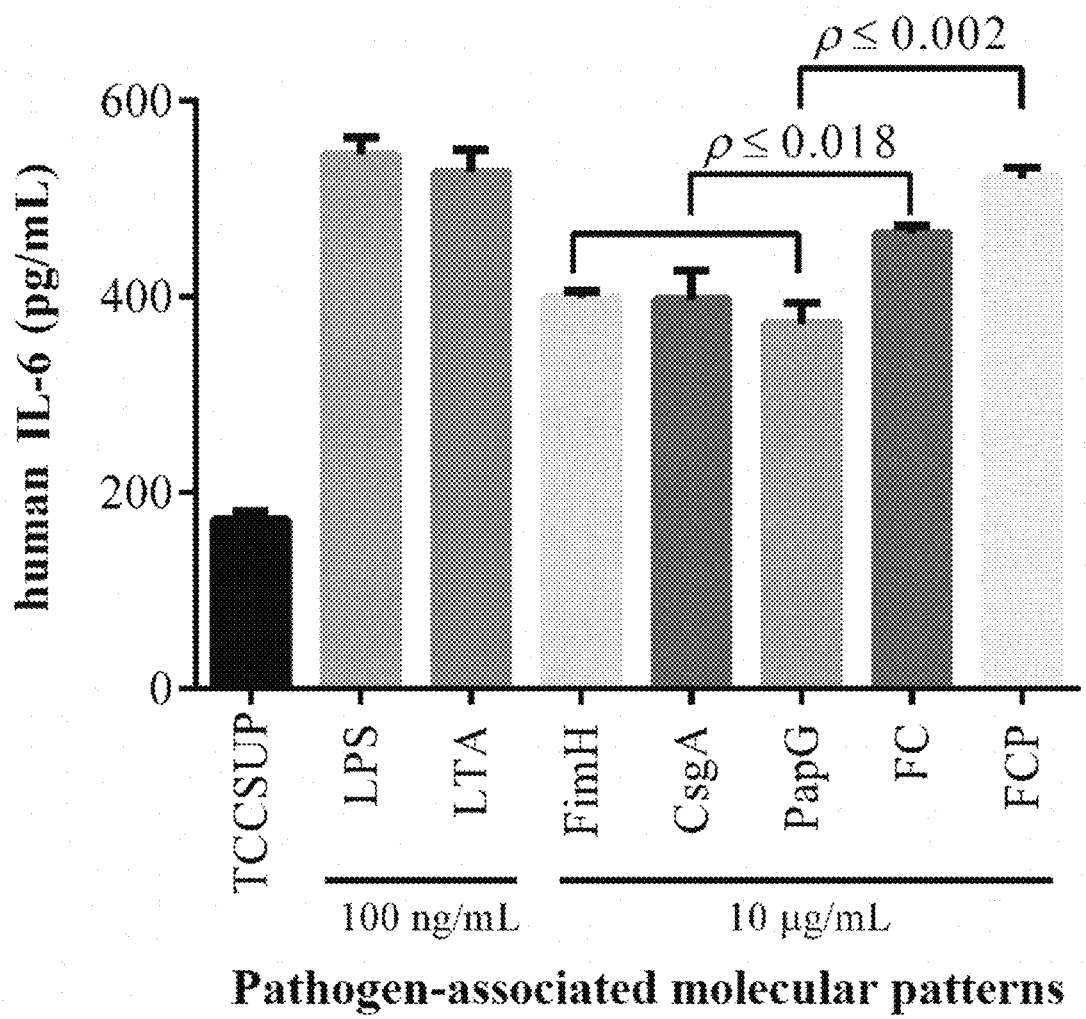
FIG. 4. Release of IL-6 stimulated by fusion proteins.
Figure 5:
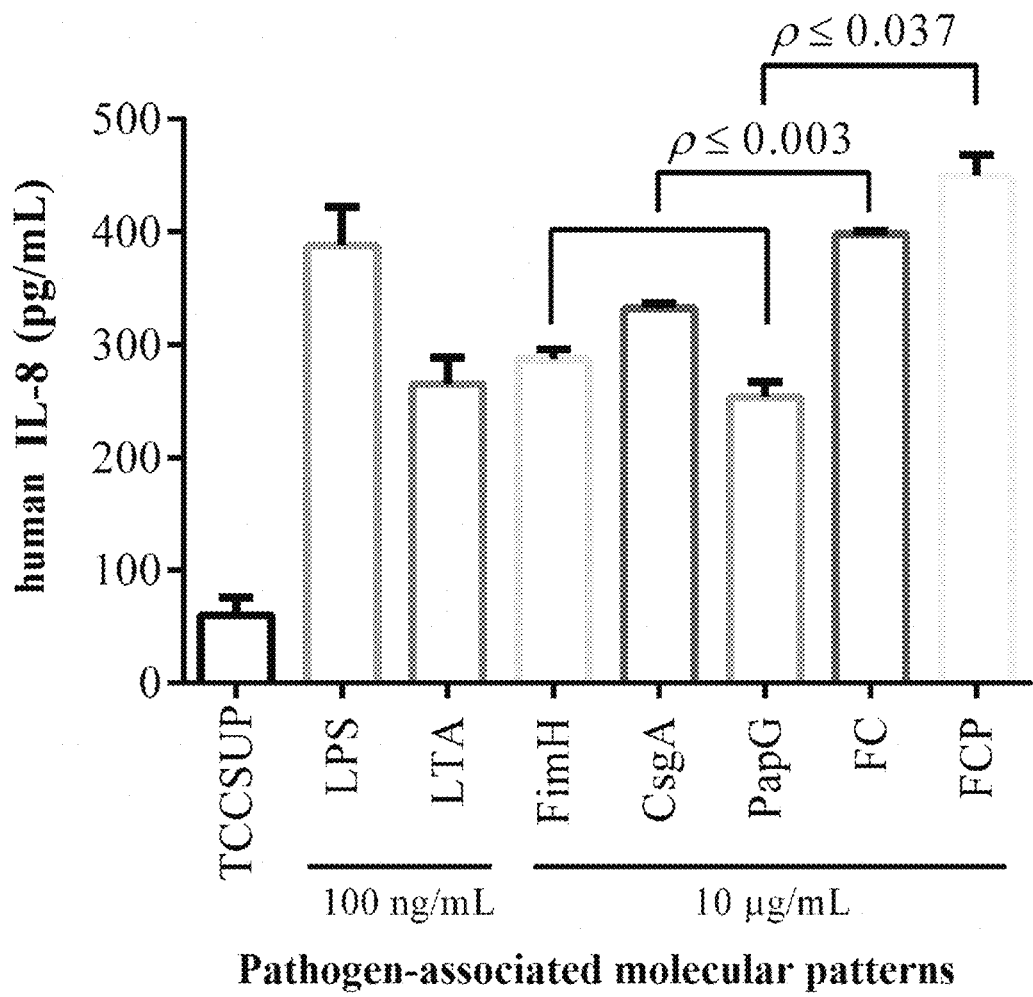
FIG. 5. Release of IL-8 stimulated by fusion proteins.

Analysis of bioactivity. The expression of TLR2 and TLR4 in HTB5 bladder cells [American Type Culture Collection (ATCC), Manassas, Va., USA] were analyzed by flow cytometry using human TLR2 fluorescein-conjugated (R&D Systems, Inc., Minneapolis, USA) and human TLR4/MD2 complex phycoerythrin-conjugated (Santa Cruz Biotechnology Inc., Texas, USA) antibodies. The activation of TLR by different proteins was determined by the quantification of IL-6 and IL-8 released in the supernatants of HTB5 cells. HTB5 cells were cultured in 24-well plates (Greiner, Germany) at a density of $10^5$ cells/well, incubated with 1 mL of Eagle's minimum essential medium (EMEM; ATCCR30-2003™) supplemented with 10% fetal bovine serum (SFB) from Gibco (Thermo Fisher Scientific, Waltham, Mass., USA). The induction of cytokines by HTB5 cells was detected after 6 h of incubation with 10 μg/mL of FimH, CsgA, PapG, FC and FCP proteins using enzyme-linked immunosorbent assays (ELISA) following the protocols established by BD Biosciences (SanJose, Calif., USA). Additionally, 100 ng/mL of LPS (Sigma-Aldrich Corp., St. Louis, Mo., USA) of E. coli 0111:B4 and 100 ng/mL of S. aureus LTA (Sigma-Aldrich Corp., St. Louis, Mo., USA) were used as control for the induction of TLR4 and TLR2, respectively. The ability to stimulate the release of IL6 and IL8 in human bladder cells by the fusion proteins are described in FIGS. 4 and 5, respectively.

Figure 6:
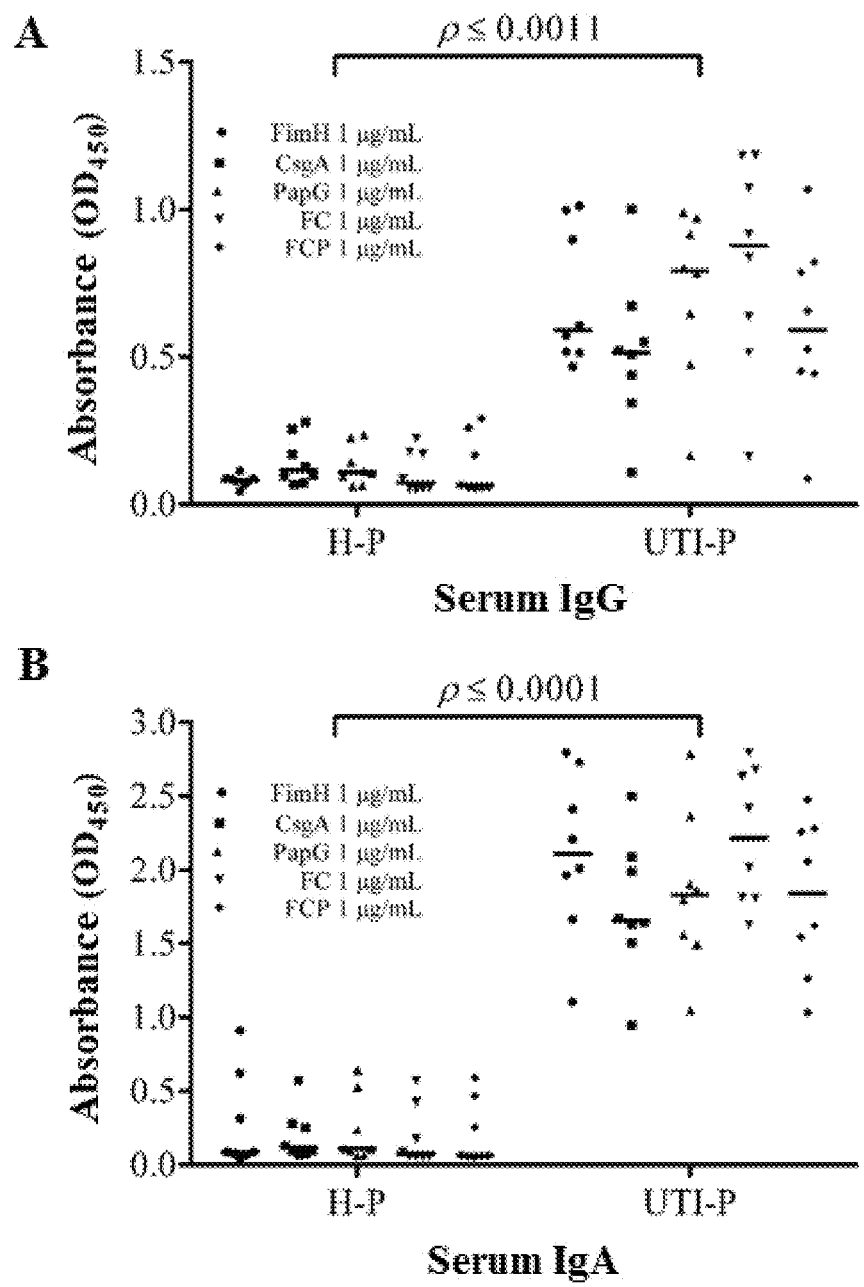
FIG. 6. Detection of IgG and IgA antibodies against the fusion proteins in the serum of healthy (H-P) and UTI (UTI-P) patients by means of ELISA assays.
Figure 7:
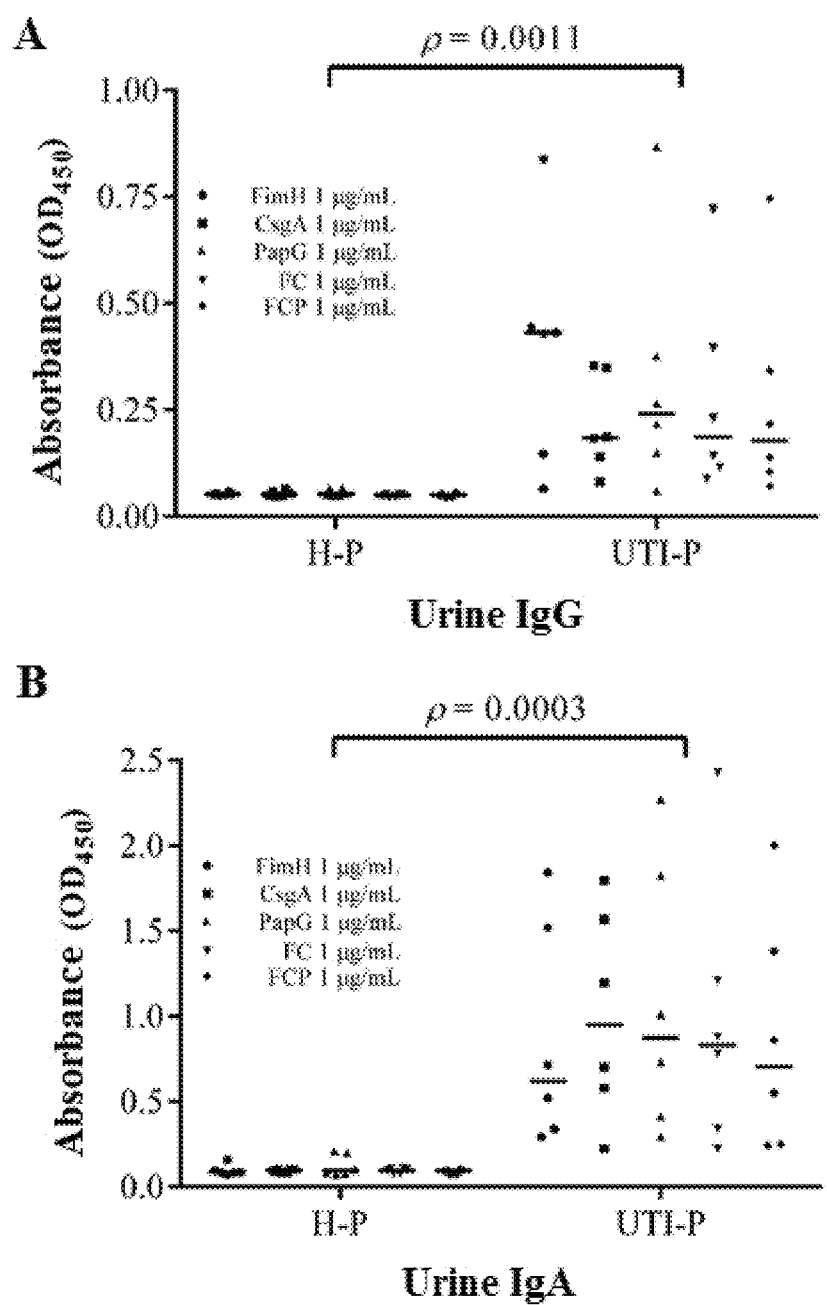
FIG. 7. Detection of IgG and IgA antibodies against fusion proteins in urines of H-P and UTI-P by ELISA assays.

Antigenicity of fusion proteins. Sera and urine samples were obtained from the Central Clinical Laboratory of the Children's Hospital of Mexico "Federico Gomez" (HIMFG) of 14 patients with UTI (UTI-P) and 14 healthy patients (H-P). The inclusion criteria for UTI-P were: UTI symptoms, urine culture with 100,000 CFU/mL of E. coli, leukocyte esterase and/or nitrite in urine. The samples were centrifuged at 7835 g for 5 min and filtered with a Durapore 0.22 μm membrane (Merck Millipore, Darmstadt, Germany). The IgG and IgA antibody titers against the FimH, CsgA, PapG, FC and FCP proteins were determined by ELISA using the 1:50 serum and 1:10 urine diluted samples. The study was approved by the research (Dr. Onofre Munoz Hernandez), ethics (Dr. Amparo Faure Fontenla) and biosafety (Dr. Herlinda Vera Hermosillo) committees of the HIMFG under the grant numbers HIM/2014/022 and HIM/2016/027. The antigenic capacity assessment of fusion proteins in UTI-P serum and urine is described in FIGS. 6 and 7, respectively.

Generation of polyclonal antibodies in rabbit. 5-6-month age New Zealand rabbits were obtained from the animal facility of the UNAM's Cellular Physiology Institute. The rabbits were subcutaneously immunized with 200 μg of the proteins FimH, CsgA, PapG, FC and FCP spiked with Freund's complete adjuvant. Subsequently, the rabbits were immunized three times (days 21, 28 and 37) with 100 μg of each protein in incomplete Freund's adjuvant and bleeded by cardiac puncture on day 40. The blood obtained was centrifuged at 7835 g for 5 min and the serum was stored at −70° C. until use. The sera were absorbed using the CFT073 csgA::Km/fimH::Cm mutant strain generated by the working group following the single step gene inactivation method (Datsenko and Wanner, 2000). The sera with anti-PapG and anti-FCP antibodies were absorbed with the same mutant strain grown under conditions where it does not express P fimbriae, which was confirmed by RT-PCR. The sera were inactivated by heat at 56° C. for 30 min and titrated by ELISA using serial dilutions of 1:10 to 1:100,000 against the specific proteins.

Figure 8:
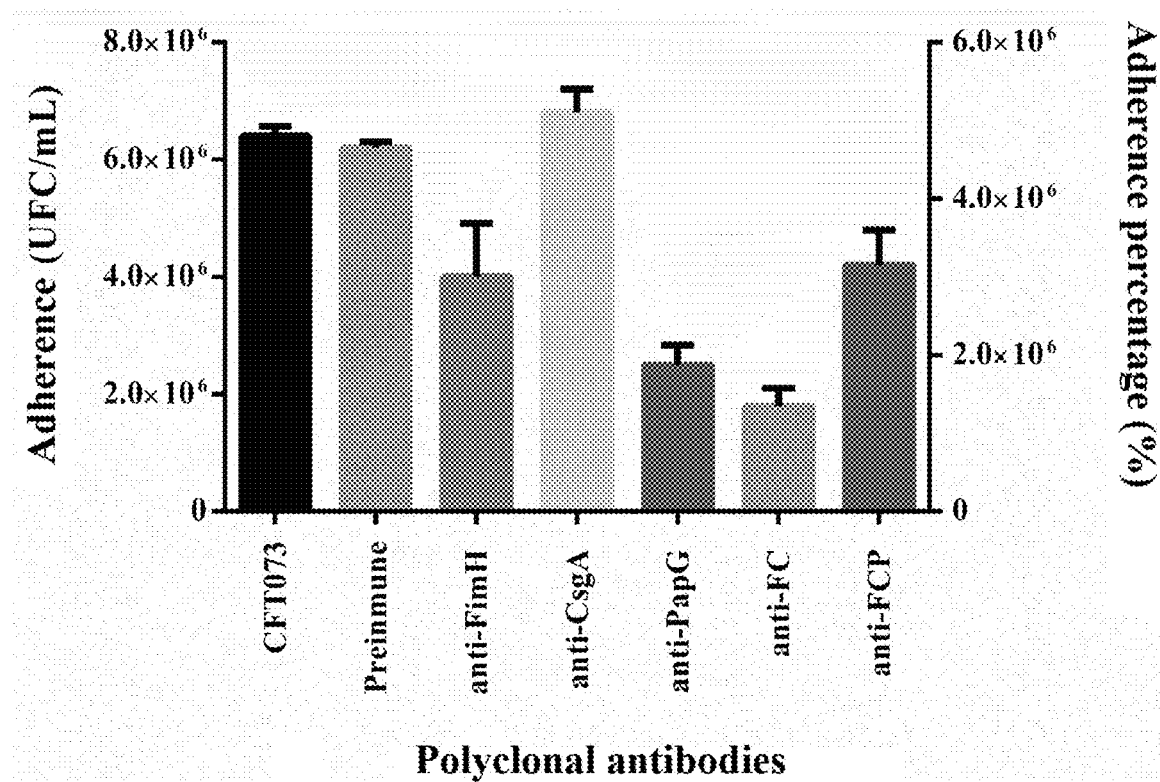
FIG. 8. Polyclonal antibodies generated against fusion proteins reduce bacterial adhesion to human bladder cells.

Adhesion inhibition assays. HTB5 cells were cultured in 24-well plates at $10^5$ cells/well in 1 mL of EMEM supplemented with 10% FBS until reaching an 80% confluence. Previously, an aliquot of a culture of strain CFT073 was grown overnight in LB at 37° C. and an aliquot (1:100 dilution) of the culture was incubated until obtaining an $OD_{600nm}$ of 1.0. Bacterial cultures were treated with 2.5% mannose at 37° C. for 1 h under shaking. Cell monolayers were infected with $10^7$ bacteria at a MOI of 100 and incubated for 3 hours at 37° C. in 5% $CO_2$. A previous step was performed for the adhesion inhibition assay using the UPEC CFT073 strain incubated with polyclonal antibodies raised in rabbit anti FimH, CsgA, PapG, FC and FCP at a final concentration of 50% at 37° C. for 2 h. The infected cells were washed 3 times with sterile PBS and subsequently treated with 1 mL of PBS with 0.1% Triton X-100. Adhered bacteria were counted (CFU/mL) using the previously described method (Hannan and Hunstad, 2016). The levels of inhibition of E. coli CFT073 to bladder cells by the antibodies raised against the fusion proteins are described in FIG. 8.

Tests and Results

The fusion proteins activate the release of IL-6. The human bladder HTB5 cells were treated with 10 µg/mL of each of the fusion proteins, and the release of IL-6 in the supernatants was detected by ELISA. The maximum induction of IL-6 was generated with the FCP fusion protein, which exhibited significant differences ($p \le 0.002$) compared with the FC, FimH, CsgA and PapG proteins. The FC protein also caused a significant increase ($p \le 0.018$) in the level of IL-6 compared to the FimH, CsgA and PapG proteins. The bars represent the mean±standard deviation (SD) of three independent experiments. Lipopolysaccharide (LPS) and lipoteichoic acid (LTA) at concentrations of 100 ng/mL were used as controls. The results are described in FIG. 4.

The fusion proteins activate the release of IL-8. The HTB5 cells were treated with 10 µg/mL of each of the fusion proteins, and the release of IL-8 in the supernatants was detected by ELISA. A significant increase ($p \le 0.037$) in the release of IL-8 was induced by the FCP protein compared to FC, FimH, CsgA and PapG proteins. The FC protein also caused a significant increase ($p \le 0.003$) in the release of IL-8 compared to the FimH, CsgA and PapG proteins. The bars represent the mean±SD of three independent experiments. LPS and LTA (100 ng/mL) were used as controls. The results are described in FIG. 5.

Detection of IgG and IgA antibodies in the serum of patients with UTI. A significant increase ($p \le 0.0011$) in the IgG antibodies in UTI-P sera was detected compared to the IgG values in H-P serum. IgA antibodies in UTI-P sera were significantly increased ($p \le 0.0001$) compared to IgA antibodies in H-P sera. Interestingly, UTI-P serum IgA antibody values showed increases when compared with IgG antibodies in H-P sera. The ELISA assays were performed in triplicate using three different samples and 1 µg/mL of each protein. The dots represent individual values and the bars represent the median of the data. The results are described in FIG. 6.

Detection of IgG and IgA antibodies in UP urines. A significant increase ($p=0.0011$) in IgG antibodies in UTI-P urines was detected compared to the IgG antibody values in H-P. IgA antibodies in UTI-P urines were significantly increased ($p=0.0003$) compared to IgA antibodies in H-P urines. Interestingly, the IgA antibody values in UTI-P urine showed increases when compared with the IgG antibodies in H-P urine. The ELISA assays were performed in triplicate using three different samples and 1 µg/mL of each protein. The dots represent individual values and the bars represent the median of the data. The results are described in FIG. 7.

Polyclonal antibodies against fusion proteins reduce bacterial adherence. The *E. coli* strain CFT073 was incubated with sera from rabbits immunized with FimH, CsgA, PapG, FC, FCP proteins (1:1, V/V) and HTB5 bladder cells (MOI 100) for 2 h. Polyclonal rabbit antibodies favored the reduction in bacterial adherence (CFU/mL, %) compared to the basal adhesion of CFT073 strain and a mixture of pre-immune sera. The bars represent the mean±SD of three independent experiments. $p=0.0011$, *$p=0.0002$ and ****$p<0.0001$. The results are described in FIG. 8.

CONCLUSION

The invention is based on the design of a fcpfc fusion template gene which allows to generate different fusion proteins, such as: monomeric, dimeric and trimeric proteins. The different bioinformatic analyzes allowed to select the FC dimeric and FCP trimeric proteins. These proteins may be potential in the future for the generation of a vaccine against UTIs by UPEC. However, the possibility of generating variants in the dimeric and trimeric fusion proteins will allow to obtain stable proteins with a correct folding for their evaluation as biomolecules for diagnosis and/or vaccines.

REFERENCES

Asadi Karam, M. R., Oloomi, M., Mandavi, M., Habibi, M., and Bouzari, S. (2013). Vaccination with recombinant FimH fused with flagellin enhances cellular and humoral immunity against urinary tract infection in mice. Vaccine 31, 1210-1216.

Ashkar, A. A., Mossman, K. L., Coombes, B. K., Gyles, C. L., and Mackenzie, R. (2008). FimH adhesin of type 1 fimbriae is a potent inducer of innate antimicrobial responses which requires TLR4 and type 1 interferon signalling. PLoS Pathog. 4, e1000233.

Bens, M., Vimont, S., Ben Mkaddem, S., Chassin, C., Goujon, J.-M., Balloy, V., Chignard, M., Werts, C., and Vandewalle, A. (2014). Flagellin/TLR5 signalling activates renal collecting duct cells and facilitates invasion and cellular translocation of uropathogenic *Escherichia coli*. Cell. Microbiol. 16, 1503-1517.

Fischer, H., Yamamoto, M., Akira, S., Beutler, B., and Svanborg, C. (2006). Mechanism of pathogen-specific TLR4 activation in the mucosa: fimbriae, recognition receptors and adaptor protein selection. Eur. J. Immunol. 36, 267-277.

Habibi, M., Asadi Karam, M. R., Shokrgozar, M. A., Oloomi, M., Jafari, A., and Bouzari, S. (2015a). Intranasal immunization with fusion protein MrpH·FimH and MPL adjuvant confers protection against urinary tract infections caused by uropathogenic *Escherichia coli* and *Proteus mirabilis*. Mol. Immunol. 64, 285-294.

Habibi, M., Asadi Karam, M. R., and Bouzari, S. (2015b). In silico design of fusion protein of FimH from uropathogenic *Escherichia coli* and MrpH from *Proteus mirabilis* against urinary tract infections. Adv. Biomed. Res. 4, 217.

Hannan, T. J., and Hunstad, D. A. (2016). A Murine Model for *Escherichia coli* Urinary Tract Infection. Methods Mol. Biol. Clifton N.J. 1333, 159-175.

Huleatt, J. W., Jacobs, A. R., Tang, J., Desai, P., Kopp, E. B., Huang, Y., Song, L., Nakaar, V., and Powell, T. J. (2007). Vaccination with recombinant fusion proteins incorporating Toll-like receptor ligands induces rapid cellular and humoral immunity. Vaccine 25, 763-775.

Hung, C.-S., Dodson, K. W., and Hultgren, S. J. (2009). A murine model of urinary tract infection. Nat. Protoc. 4, 1230-1243.

Karam, M. R. A., Oloomi, M., Mandavi, M., Habibi, M., and Bouzari, S. (2013). Assessment of immune responses of the flagellin (FliC) fused to FimH adhesin of Uropathogenic *Escherichia coli*. Mol. Immunol. 54, 32-39.

Lane, M. C., and Mobley, H. L. T. (2007). Role of P-fimbrial-mediated adherence in pyelonephritis and persistence of uropathogenic *Escherichia coli* (UPEC) in the mammalian kidney. Kidney Int. 72, 19-25.

Lane, M. C., Alteri, C. J., Smith, S. N., and Mobley, H. L. T. (2007). Expression of flagella is coincident with uropathogenic *Escherichia coli* ascension to the upper urinary tract. Proc. Natl. Acad. Sci. U.S.A. 104, 16669-16674.

Langermann, S., Möllby, R., Burlein, J. E., Palaszynski, S. R., Auguste, C. G., DeFusco, A., Strouse, R., Schenerman, M. A., Hultgren, S. J., Pinkner, J. S., et al. (2000).

Vaccination with FimH adhesin protects cynomolgus monkeys from colonization and infection by uropathogenic *Escherichia coli*. J. Infect. Dis. 181, 774-778.

Laskowski, R. A., MacArthur, M. W., and Thornton, J. M. (1998). Validation of protein models derived from experiment. Curr. Opin. Struct. Biol. 8, 631-639.

Ledesma, M. A., Ochoa, S. A., Cruz, A., Rocha-Ramírez, L. M., Mas-Oliva, J., Eslava, C. A., Girón, J. A., and Xicohtencatl-Cortes, J. (2010). The hemorrhagic *coli* pilus (HCP) of *Escherichia coli* O157:H7 is an inducer of proinflammatory cytokine secretion in intestinal epithelial cells. PloS One 5, e12127.

Li, G., Huang, Z., Zhang, C., Dong, B.-J., Guo, R.-H., Yue, H.-W., Yan, L.-T., and Xing, X.-H. (2016). Construction of a linker library with widely controllable flexibility for fusion protein design. Appl. Microbiol. Biotechnol. 100, 215-225.

Martinez, J. J., Mulvey, M. A., Schilling, J. D., Pinkner, J. S., and Hultgren, S. J. (2000). Type 1 pilus-mediated bacterial invasion of bladder epithelial cells. EMBO J. 19, 2803-2812.

Pedretti, A., Villa, L., and Vistoli, G. (2004). VEGA—an open platform to develop chemo-bio-informatics applications, using plug-in architecture and script programming. J. Comput. Aided Mol. Des. 18, 167-173.

Puigbò, P., Guzmán, E., Romeu, A., and Garcia-Vallvé, S. (2007). OPTIMIZER: a web server for optimizing the codon usage of DNA sequences. Nucleic Acids Res. 35, W126-W131.

Rapsinski, G. J., Wynosky-Dolfi, M. A., Oppong, G. O., Tursi, S. A., Wilson, R. P., Brodsky, I. E., and Tükel, C. (2015). Toll-like receptor 2 and NLRP3 cooperate to recognize a functional bacterial amyloid, curli. Infect. Immun. 83, 693-701.

Saldaña, Z., Xicohtencatl-Cortes, J., Avelino, F., Phillips, A. D., Kaper, J. B., Puente, J. L., and Giron, J. A. (2009). Synergistic role of curli and cellulose in cell adherence and biofilm formation of attaching and effacing *Escherichia coli* and identification of F is as a negative regulator of curli. Environ. Microbiol. 11, 992-1006.

Savar, N. S., Jahanian-Najafabadi, A., Mandavi, M., Shokrgozar, M. A., Jafari, A., and Bouzari, S. (2014). In silico and in vivo studies of truncated forms of flagellin (FliC) of enteroaggregative *Escherichia coli* fused to FimH from uropathogenic *Escherichia coli* as a vaccine candidate against urinary tract infections. J. Biotechnol. 175, 31-37.

Sen, T. Z., Jernigan, R. L., Garnier, J., and Kloczkowski, A. (2005). GOR V server for protein secondary structure prediction. Bioinforma. Oxf. Engl. 21, 2787-2788.

Snyder, J. A., Haugen, B. J., Lockatell, C. V., Maroncle, N., Hagan, E. C., Johnson, D. E., Welch, R. A., and Mobley, H. L. T. (2005). Coordinate expression of fimbriae in uropathogenic *Escherichia coli*. Infect. Immun. 73, 7588-7596.

Tükel, C., Nishimori, J. H., Wilson, R. P., Winter, M. G., Keestra, A. M., van Putten, J. P. M., and Bäumler, A. J. (2010). Toll-like receptors 1 and 2 cooperatively mediate immune responses to curli, a common amyloid from enterobacterial biofilms. Cell. Microbiol. 12, 1495-1505.

Wiederstein, M., and Sippl, M. J. (2007). ProSA-web: interactive web service for the recognition of errors in three-dimensional structures of proteins. Nucleic Acids Res. 35, W407-W410.

Wilkins, M. R., Gasteiger, E., Bairoch, A., Sanchez, J. C., Williams, K. L., Appel, R. D., and Hochstrasser, D. F. (1999). Protein identification and analysis tools in the ExPASy server. Methods Mol. Biol. Clifton N.J. 112, 531-552.

Yang, J., Yan, R., Roy, A., Xu, D., Poisson, J., and Zhang, Y. (2015). The I-TASSER Suite: protein structure and function prediction. Nat. Methods 12, 7-8.

Zhang, Y., and Skolnick, J. (2005). TM-align: a protein structure alignment algorithm based on the TM-score. Nucleic Acids Res. 33, 2302-2309.

Having claimed the invention as above, it is claimed as property what is contained in the following claims:

1. A fusion protein characterized in that it includes a FimH adhesin covalently linked to a PapG and CsgA adhesins of uropathogenic *Escherichia coli* (*E. coli*), which comprises or consisting of SEQ ID NO: 2.

2. The fusion protein of claim 1 for use as a biomolecule forming part of a vaccine against urinary tract infections.

3. The fusion protein of claim 1 for use as a molecule for diagnosis of urinary tract infections by uropathogenic *Escherichia coli*.

4. The fusion protein of claim 1 for use in stimulating an immune system in an animal model.

5. A process for obtaining a template fusion gene of the fusion protein of claim 1, characterized in that the sequences of fimH, csgA, and papG of the *E. coli* strain CFT073 were obtained by a consensus nucleotide sequences that are fused with codons of repeats of the amino acid sequence according to SEQ ID NO: 9 to generate the template fusion gene, and subsequently they are cloned into a cloning or expression vector, which was used for an amplification of a monomeric, dimeric and trimeric genes.

6. A fusion protein characterized in that it includes covalently linked adhesins of uropathogenic *Escherichia coli* (*E. coli*), which comprises or consisting of SEQ ID NO: 2, wherein the fusion protein is a dimeric variant selected from the group consisting of FimH-CsgA (FC), CsgA-PapG (CP), and PapG-FimH (PF).

7. A fusion protein characterized in that it includes covalently linked adhesins of uropathogenic *Escherichia coli* (*E. coli*), which comprises or consisting of SEQ ID NO: 2, wherein the fusion protein is a trimeric variant selected from the group consisting of FimH-CsgA-PapG (FCP), CsgA-PapG-FimH (CPF), and PapG-FimH-CsgA (PFC).

8. The fusion protein of claim 6, for their use as biomolecules forming part of a vaccine potential against urinary tract infections.

9. The fusion protein of claim 6, for their use as biomolecules for diagnosing urinary tract infections by *Escherichia coli*.

10. The fusion protein of claim 6, for their use in stimulating an immune system in an animal model.

11. The fusion protein of claim 7, for their use as biomolecules forming part of a vaccine potential against urinary tract infections.

12. The fusion proteins of claim 7, for their use as biomolecules for diagnosing urinary tract infections by *Escherichia coli*.

13. The fusion proteins of claim 7, for their use in stimulating an immune system in an animal model.

* * * * *